(12) United States Patent
Frey et al.

(10) Patent No.: US 8,864,664 B2
(45) Date of Patent: Oct. 21, 2014

(54) MEDICAL DEVICE WITH A COLLECTION CHANNEL FOR A BODILY FLUID

(75) Inventors: Stephan-Michael Frey, Griesheim (DE); Marc Arnold, Gorxheimertal (DE); Tobias Brugger, Korb (DE); Jürgen Braun, Ehningen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 550 days.

(21) Appl. No.: 13/195,368

(22) Filed: Aug. 1, 2011

(65) Prior Publication Data

US 2012/0035447 A1  Feb. 9, 2012

(30) Foreign Application Priority Data

Aug. 4, 2010 (EP) .................................... 10171883

(51) Int. Cl.
*A61B 5/00* (2006.01)
*A61B 5/145* (2006.01)

(52) U.S. Cl.
CPC ............. *A61B 5/6849* (2013.01); *A61B 5/6833* (2013.01); *A61B 5/4839* (2013.01); *A61B 5/14532* (2013.01)
USPC ............................ 600/300; 600/347; 600/365

(58) Field of Classification Search
USPC .................................. 600/316, 347, 365, 583
See application file for complete search history.

(56) References Cited

U.S. PATENT DOCUMENTS

| | | | | |
|---|---|---|---|---|
| 4,106,497 | A * | 8/1978 | Percarpio ...................... | 600/579 |
| 5,951,521 | A | 9/1999 | Mastrototaro et al. | |
| 6,058,321 | A * | 5/2000 | Swayze et al. ................ | 600/310 |
| 7,125,402 | B1 * | 10/2006 | Yarger .......................... | 604/541 |
| 2006/0008389 | A1 * | 1/2006 | Sacherer et al. ............... | 422/102 |
| 2007/0106178 | A1 * | 5/2007 | Roe et al. ...................... | 600/583 |
| 2007/0232978 | A1 | 10/2007 | Castellani | |
| 2008/0140009 | A1 * | 6/2008 | Haueter et al. ................ | 604/161 |
| 2008/0275313 | A1 * | 11/2008 | Brister et al. ................. | 600/300 |
| 2008/0319416 | A1 * | 12/2008 | Yodfat et al. .................. | 604/513 |

FOREIGN PATENT DOCUMENTS

| | | |
|---|---|---|
| EP | 2 111 793 | 10/2009 |
| GB | 24490 | 7/1912 |
| WO | WO 2009/035773 | 3/2009 |

* cited by examiner

*Primary Examiner* — Etsub Berhanu
(74) *Attorney, Agent, or Firm* — Roche Diagnostics Operations, Inc.

(57) ABSTRACT

A medical device for carrying out at least one medical function. The medical device comprises at least one control part, which can be applied to a body surface of a user, and at least one functional element, which can be inserted into a body tissue of the user at at least one insertion site. The functional element can be connected to the control part. The functional element is designed to carry out at least one medical function. The control part has at least one base part with at least one supporting surface, which faces the body surface. The base part has at least one collection channel for collecting bodily fluid emerging from the insertion site.

36 Claims, 3 Drawing Sheets

MEDICAL DEVICE WITH A COLLECTION CHANNEL FOR A BODILY FLUID

RELATED APPLICATIONS

This application claims priority to EP 10 171 883.1, filed Aug. 4, 2010 which is hereby incorporated by reference in its entirety.

BACKGROUND

The invention relates to a medical device for carrying out at least one medical function and to a base part for use in such a medical device. Such medical devices and base parts are used, in particular, in the field of medical diagnostics and/or therapeutics. By way of example, the medical device may be embodied as a long-term sensor and comprise at least one sensor element, which can be inserted into a body tissue of the user, and a control part, which is connected to this sensor element and applied to a body surface of the user, in order to acquire, qualitatively and/or quantitatively, one or more analytes in a bodily fluid of the user, for example over a period of a number of days, weeks or months. Alternatively, or in addition thereto, the medical device can also be designed for therapeutic purposes and can for example be embodied as a medication device. Hence, the medical device may, for example, comprise at least one cannula, which can be inserted into a body tissue of the user, and at least one control part, which is connected to this cannula and arranged on the body surface, for example with at least one medication pump, for example in order to administer one or more medicaments into the body tissue over a relatively long period of time. Various other embodiments are possible.

Numerous medical devices with diagnostic, therapeutic or surgical functions are known. In particular, monitoring and/or influencing certain body functions, preferably monitoring one or more concentrations of certain analytes, plays a substantial role in preventing and treating various diseases such as diabetes. Without restricting further possible applications, exemplary embodiments are described below substantially with reference to blood-glucose monitoring, more particularly with reference to continuous, long-term blood-glucose monitoring over a number of hours, days, weeks or even months. However, in principle these teachings can be transferred to other types of analyte monitoring and/or to monitoring other types of body functions, and also to different fields in medicine. In particular, the invention can also be applied to medical therapeutics, for example to medication pumps such as insulin pumps.

Continuous measurements are becoming ever more established in addition to so-called point measurements of one or more analytes, in which a sample of a bodily fluid is taken from a user in a targeted fashion. Thus, for example, a continuous glucose measurement in the interstitium (also referred to as continuous monitoring [CM]) has been established in the recent past as an important method for managing, monitoring and controlling a diabetes state, for example. In general, this continuous monitoring is initially restricted to type I diabetics, i.e. diabetics who usually also wear an insulin pump. However, other user types are gradually being considered as well. By now, use is generally made of directly implanted electrochemical sensors, which are often also referred to as needle-type sensors (NTS). Here, the active sensor region is brought directly to the measurement location, which is generally arranged in the interstitial tissue and converts glucose into electric charges, for example by using an enzyme (e.g. glucose oxidase, GOD), which charges are proportional to the glucose concentration and can be used as a measurement variable. Examples of such transcutaneous measurement systems are described in U.S. Pat. No. 6,360,888 or in U.S. Publication No. 2008/0242962 A1.

Hence, current continuous monitoring systems are generally transcutaneous systems. In general, this means that the actual sensor is arranged at least partly below the skin of the user. However, a control part of the system, which is also referred to as a patch, is generally situated outside of the body of the user, i.e. outside of the human or animal body. In the process, the sensor is generally applied by means of insertion instruments and is inserted into the body tissue through a skin surface, which is likewise described in U.S. Pat. No. 6,360,888 in an exemplary fashion. Other types of insertion instruments are also known. In general, a sensor is worn for a period of approximately one week; however, longer periods of wear, for example up to one or more months, are also possible. Thereafter, the sensitivity of the sensor generally drops off as a result of influences such as, for example, enzymes being used up and/or the sensor becoming encapsulated in the body, and hence the sensor can be expected to fail. Increasing the length of the period of wear is an area of active research. However, this means that the sensor, and optionally components such as an insertion needle directly connected thereto, should be embodied as replaceable elements. Accordingly, the sensor and, in general, further replaceable components of the device constitute a so-called disposable. However, an actuation unit of the control part, which comprises expensive components of the same (such as high-resistance amplifier input stages and/or potentiostats and/or similar active elements), is generally reused and so the device often comprises at least one reusable component.

In the case of implantable sensors, the disposable generally comprises a so-called body mount, which can be affixed to a skin surface of the user. By way of example, the body mount generally contains a base part and at least one plaster in order to affix this base part onto the skin surface. The reusable, which may contain the essential parts of actuation and/or evaluation electronics for measuring the analyte concentration, is then connected to this body mount, which generally also carries the insertable sensor. However, components such as at least one battery can be arranged in the body mount itself, and so when a body mount is replaced, and a new body mount and the reusable are assembled, the device is at the same time also embodied with a new source of energy.

A general problem in the case of medical devices with insertable functional elements consists of the fact that a bodily fluid, such as e.g. blood or interstitial fluid, can emerge from the insertion site during or after the insertion, which insertion site is where the functional element or part thereof penetrates the body surface. This bodily fluid can contaminate the functional element and/or other components of the medical devices. Thus, by way of example, a bodily fluid may reach electrical contacts of a sensor element, which contacts are arranged within the control part, and may cause e.g. leakage currents or other electronic interference there.

U.S. Pat. No. 5,951,521 has disclosed an implantable subcutaneous set for assembly on a skin surface of a user. Here, a base with a cannula is used while a subcutaneous sensor is being inserted. The cannula has a lumen, within which the sensor is arranged. It is furthermore proposed to route a tube line into the interior of the cannula and into the lumen in order to suction off bodily fluid collecting in the lumen after the insertion. The tube line is provided with a connector that can for example be connected to a syringe.

U.S. Publication No. 2003/0004403 A1 has disclosed methods and devices for continuously monitoring physiologically relevant body states. Inter alia, it is proposed therein to use a so-called biointerface head (BIH), which is implanted into a body tissue. Inter alia, it is proposed, in the process, to embody the biointerface head with a hollow tube line, by means of which e.g. anti-inflammatory medicaments can be introduced into the body tissue or excessive bodily fluid can be routed out of the body tissue.

However, none of the above-described devices solves the sketched-out problem that bodily fluid emerging at the insertion site can contaminate the medical device. On the contrary, the tube connections revealed in the two aforementioned documents even lead to bodily fluid additionally being able to be guided out of the body of the user from the interior of the body tissue, which bodily fluid can contaminate the medical device outside of the body and which has to be separately disposed of there. Moreover, both documents describe a separate channel in conjunction with a sensor or a cannula, which channel requires additional space and hence makes an insertion of the sensor more difficult.

SUMMARY

Disclosed herein is a medical device with at least one functional element, which can be inserted into a body tissue of a user, which medical device avoids the disadvantages of known medical devices. More particularly, bodily fluid emerging during or after the insertion should be prevented from contaminating the medical device in a bothersome fashion or from influencing the functionality of the medical device.

A medical device for carrying out at least one medical function is proposed in a first aspect of this disclosure. Here, a medical device should be understood to mean any device that is designed to carry out at least one medical function, i.e. a function selected from a therapeutic, diagnostic and surgical function. More particularly, the medical function can be at least one diagnostic function, preferably a measuring function, and/or at least one therapeutic function, more particularly at least one medication function. In particular, provision can be made for at least one sensor function. In particular, the medical device can be embodied as a personal medical device and can be embodied to be worn on a body surface of the user. Accordingly, the medical device can for example have a volume that preferably does not exceed 1000 $cm^3$ and preferably does not exceed a volume of 50 $cm^3$, more particularly does not exceed a volume of 30 $cm^3$ or even 15 $cm^3$.

The medical device comprises at least one control part, which can be applied to a body surface of a user. Here, the control part can be applied directly onto the skin of the user or it can merely be applied indirectly onto the body surface, for example by placing in-between one or more elements such as woven-fabric layers, cloth layers, plastic layers or similar layers. However, it is particularly preferable if the medical device can be applied directly to the body surface.

Here, in general terms, a control part should be understood to mean an integral or multi-part element of the medical device, which element is designed to fulfill at least one actuation and/or evaluation function of the medical device. By way of example, this can be at least one electronic function, for example at least one measuring function. To this end, the control part can for example have at least one measuring device. Alternatively, or in addition thereto, the control part can also perform at least one other function, for example at least one micro-mechanical function and/or actuation function, for example the function of a medication pump. Other embodiments are also possible. Accordingly, the control part can, in particular, comprise at least one electronic component, more particularly at least one active electronic component, more particularly at least one high-resistance operation amplifier and/or at least one potentiostat and/or at least one integrated circuit, more particularly at least one application-specific integrated circuit (ASIC). In particular, as explained in more detail below, the control part can comprise at least one disposable and at least one reusable, wherein the disposable can for example comprise a base part (described in more detail below) and wherein the reusable can for example comprise at least one actuation unit, for example an actuation unit that comprises one or more of the above-described electronic components. Typically, no electronic components, at least no active electronic components, are arranged in the disposable, except, e.g. at least one battery and/or another type of electrical energy reservoir and/or at least one storage-medium component.

The medical device furthermore comprises a functional element, which can be inserted into a body tissue of the user at at least one insertion site. Here, a functional element should be understood to mean an element that is designed to carry out and/or support the at least one medical function. In particular, the functional element can comprise at least one measuring element, for example at least one sensor element for qualitatively and/or quantitatively acquiring at least one analyte, for example at least one metabolite, in at least one bodily fluid of the user. In particular, the insertable functional element can comprise at least one electrochemical sensor. Alternatively, or in addition thereto, the insertable functional element can however also comprise at least one actuator and/or at least part of a medication device, for example a cannula. Various examples are mentioned in more detail below. In general, within the scope of this disclosure, an element is considered insertable if this element can be wholly or partly introduced into a body tissue of the user, wherein e.g. transcutaneous or even subcutaneous introductions are possible. In particular, the functional element can comprise a biocompatible surface, for example a surface that is designed to remain in the body tissue for a period of a number of hours, a number of days, a number of weeks or even a number of months, without causing inflammatory responses and/or allergic reactions, and/or without exerting toxic influences on the body tissue. By way of example, the insertable functional element may comprise at least one inert coating for this purpose. Other embodiments of insertable functional elements are also possible. In particular, the insertable functional element can be embodied such that, in the inserted state, it is subdivided into an inserted part and a part extending out of the body tissue through the body surface of the body. Thus, the insertable functional element can for example be embodied as an elongate functional element, for example in the form of a needle-type sensor and/or in the form of a cannula. Various other embodiments are possible.

The functional element can be connected to the control part, which can comprise the option of producing a connection, or else an already connected state. Thus, the functional element can, in particular, be connected to a disposable and/or a reusable of the control part. The term connectivity in principle comprises force-fit and/or bonded and/or interlocking connections. Combinations of the aforementioned connections are also possible. Thus, the functional element can for example be embodied to be connected to a base part of the control part via at least one force-fit and/or interlocking first connection, and to be subsequently connected to an actuation unit of the control part over at least one further force-fit and/or interlocking connection. Here, the term connectivity comprises the option of a reversible connectivity. Furthermore, the term "connectable" also comprises an embodiment in which the insertable functional element is permanently connected to the control part.

The functional element is embodied to carry out at least one medical function. In respect of the medical function, reference can be made to the above description of possible medical functions of the medical device. By way of example, the medical function can be a measurement function and/or an actuator function, for example a sensor function, more particularly an electrochemical sensor function, and/or a medication function, for example the function of administering and/or applying a medicament, for example by means of at least one cannula. Other embodiments are also possible.

The control part has at least one base part with at least one supporting surface, which faces the body surface. In the use-state of the medical device, this supporting surface can lie, for example directly or indirectly, on a body surface of the user, for example in the abdominal region, in the arm region or in the back region of the human or animal user. In particular, the supporting surface can substantially be embodied as a flat supporting surface. However, in principle, curved or rough supporting surfaces are also possible. By way of example, the supporting surface can be embodied to be substantially flat, with roughness that preferably does not exceed 2-3 mm and/or it can have an area that is no less than 2 cm$^2$, for example 2-50 cm$^2$, preferably 3-10 cm$^2$. In particular, the base part can be embodied as a plastic component and/or as a metallic component. By way of example, the base part can be produced as a substantially rigid injection-molded component made of a thermoplastic, wherein "substantially rigid" is understood to mean an element that does not undergo macroscopic deformation, at least not under the influence of its own weight and preferably not when forces that are usual during use act thereon either. However, in principle, other embodiments are also possible.

In order to solve the above-described problem, the base part can have at least one collection channel for collecting bodily fluid emerging from the insertion site. Here, within the scope of this disclosure, collecting can be understood to mean any type of complete or partial filling of the collection channel with the bodily fluid, which collection can take place on a temporary or permanent basis. Thus, the collection channel can act as a reservoir for temporary or permanent collection, or else it can merely serve for discharging the bodily fluid, for example under the action of capillary forces and/or other forces, e.g. the weight of the bodily fluid. Here, a collection channel is understood to be a channel, which is surrounded on all sides, or at least on three sides, by channel walls and which is designed to guide emerging bodily fluid, preferably to guide it away from the insertion site. In contrast to the above-described prior art, the collection channel should be designed to collect bodily fluid emerging from the insertion site, and to preferably guide it away from the latter, whereas the prior art has merely disclosed devices in which bodily fluid is guided out of the interior of the body tissue. Accordingly, the collection channel can for example have at least one channel opening, through which the bodily fluid can enter the collection channel and which is preferably no further away from the insertion site than 10 mm, more particularly no more than 7 mm, and particularly preferably no more than 5 mm, or even no more than 3 mm or no more than 2 mm. In particular, the collection channel can at least partly be formed in the supporting surface. More particularly, the collection channel can be designed to be parallel to the supporting surface, at least in part, or can have an angle with respect to the supporting surface of no more than 20°, preferably of no more than 10° and particularly preferably no more than 5°. Accordingly, the collection channel can be arranged substantially parallel to the skin surface, for example in a state in which the supporting surface is applied directly or indirectly to a skin surface of the user, wherein, for example, it is still possible to tolerate the aforementioned angular deviations. In particular, the collection channel can be opened towards the supporting surface, for example in the form of an at least partly opened channel. Thus, the collection channel can for example comprise at least one depression in the supporting surface, which depression could have been introduced into the supporting surface by means of, for example, an injection mold or another shaping tool or by means of a subsequent introduction, for example by means of cutting methods and/or laser methods. However, as an alternative or in addition to a collection channel opened in a direction perpendicular to the direction of longitudinal extent, there can in principle also be a collection channel that is closed on all sides perpendicular to the direction of longitudinal extent. However, the embodiment of the collection channel as an opened channel, for example at least in part as a gap and/or depression, is particularly preferred.

The supporting surface can be covered by at least one fixing element, particularly on the side facing the body surface, which fixing element serves to affix the base part to the body surface. This fixing element can be part of the medical device, more particularly the control part and therein it can preferably be part of the disposable. The fixing element, for example a plaster, can more particularly wholly or partly cover the supporting surface and can optionally also extend laterally beyond the supporting surface. Accordingly, the fixing element can be arranged between the collection channel and the skin surface of the user, particularly in at least one or more regions. More particularly, the fixing element can comprise at least one plaster with a sticky side facing the body surface. However, in principle, it is also possible to affix the base part to the body surface by other means, for example by providing the base part itself with a self-adhesive supporting surface. If the fixing element, more particularly the plaster, completely or partly covers the supporting surface, the fixing element can at least partly cover the collection channel. This affords the possibility of wholly or partly closing the collection channel, in particular an open collection channel, by the fixing element. By way of example, the fixing element can be produced from a textile material and/or a plastic material and/or a paper material. Thus the fixing element itself can for example have absorbent properties and can, for example, also be embodied to collect bodily fluid, supplied to it by the collection channel. Alternatively, or in addition thereto, the side of the fixing element facing the supporting surface can also be designed to be inert and non-absorbent for the bodily fluid such that, for example, this side can form a complete channel wall of the collection channel, which channel wall does not absorb the bodily fluid such that the bodily fluid continues to be guided through the collection channel. In general, the channel wall can have a planar design, for example perpendicular to the supporting surface. However, other embodiments of the channel wall are also possible, for example angled designs and/or round designs and/or stepped designs of the channel wall, for example with a step.

The functional element can be designed to carry out and/or at least support the at least one medical function of the medical device. Thus, in particular, the functional element can be selected from the following: a sensor element for acquiring at least one body state of the user; a sensor element for acquiring at least one analyte in a bodily fluid of the user; an actuator for influencing at least one body state of the user; a medication device for applying at least one active ingredient into a body tissue of the user. Combinations of the aforementioned embodiments are also possible because, for example, acquiring an analyte at the same time also contains the acquisition of a body state of the user or because, for example, a medication device can also be considered or used as an actuator for influencing a body state. It is also possible to combine at least one sensor element with at least one medication device.

Further possible embodiments of the invention relate to the possible embodiments of the collection channel. It is possible to provide one or more collection channels. In particular, the collection channel can end at at least one edge of the supporting surface. Thus, the supporting surface, for example, can have a polygonal and/or a round, for example an oval, circumference with a circumferential edge, on which the at least one collection channel ends. This allows the collection channel to extend away from e.g. the insertion site or an opening of the collection channel in the vicinity of the insertion site and up to an edge of the supporting surface on the circumference of the supporting surface in order to guide the bodily fluid a long way away from the insertion site.

In particular, the medical device can be designed to affix the insertable functional element in an inserted state that is at an angle to the body surface. By way of example, the functional element can enter the body tissue at the insertion site at an angle of 45°, wherein e.g. deviations of preferably no more than +/−20°, more particularly of no more than +/−10°, are also tolerable. In particular, the collection channel can be arranged on the body surface at an angle to a projection of the inserted functional element. By way of example, the collection channel can be arranged on the body surface at an angle of substantially 90° to the projection of the inserted functional element, preferably at a substantially right angle, that is to say for example at an angle between 70° and 110°, more particularly between 80° and 100°, and particularly preferably at an angle of about 90°.

The base part can more particularly have at least one opening in the supporting surface, which opening can be wholly or partly surrounded by the base part. By way of example, the opening can have a polygonal, a round and, in particular, an oval design. The insertable functional element penetrates this opening in the inserted state. The collection channel then preferably extends away from the opening, i.e. from an inner border of the opening facing the insertion site. By way of example, the collection channel can extend away from the opening to an outer edge of the supporting surface. The collection channel can have an integral or multi-part design. In particular, the collection channel can extend away from the opening in at least two directions. By way of example, the collection channel can extend in two opposing directions, which extend substantially perpendicular to the projection of the functional element, in the inserted state, on the body surface, as per the definition above. As a result of this extent in at least two directions, it is also possible to ensure a reversibility of an application to a body surface, for example by allowing both a right-handed application in a first orientation and also a left-handed application in a second orientation.

It is particularly preferable for at least one sidewall of the collection channel, which sidewall restricts the spread of the bodily fluid in a direction parallel to the supporting surface, to open into the opening and/or to at least partly surround the opening. The opening can also be arranged entirely within the collection channel. In a region away from the opening, for example at a distance of at least 3 mm from the opening, the collection channel may have sidewalls, which, in particular, are substantially parallel. Furthermore, the collection channel can, in particular, also have at least one enlargement as a reservoir for the bodily fluid. By way of example, provision can be made for one or more enlargements. However, alternatively, the collection channel can, away from the opening, also be designed as only a collection channel with parallel sidewalls. In particular, the collection channel can be embodied as a capillary channel, i.e. as a channel that develops capillary forces in the case of typical bodily fluids such as blood or interstitial fluid. In particular, the collection channel can have a depth perpendicular to the supporting surface, wherein the depth can be between 0.05 mm and 3 mm, more particularly between 0.1 mm and 2 mm, and particularly preferably between 0.2 mm and 1 mm, for example 0.5 mm. At its narrowest point, for example at a point at which the sidewalls run substantially parallel, the collection channel can in particular have a width of between 0.2 mm and 10 mm, more particularly between 0.3 mm and 5 mm, and particularly preferably a width of between 0.5 mm and 2 mm, for example 1 mm.

There are different options which can be implemented for forming the collection channel in the base part, more particularly in the supporting surface. Thus, for example, the base part can have at least one projection, for example an elongate projection, which extends away from the support surface and which can form at least part of at least one sidewall of the collection channel. By way of example, this projection can have a height of between 0.2 mm and 2 mm, more particularly between 0.5 mm and 1 mm. Such a projection, which can for example be embodied as a bead, ridge or rib, and which can, in particular, act as an elongate sidewall or a part thereof, can easily be produced from a plastic-technical point of view. Alternatively, or in addition thereto, the projection can, for example, also serve for further purposes. Thus, the at least one projection can, for example, also have a sealing effect and can for example be designed as a sealing projection or sealing rib. Alternatively, or in addition thereto, the projection can also serve as a connection element of the supporting surface to one or more further elements, for example for connecting the supporting surface to the fixing element, for example a plaster and/or a nonwoven fabric. Thus, for example, the at least one projection can be adhesively bonded or welded to the fixing element, or it can be connected to the latter in another fashion.

As an alternative or in addition to the at least one projection as a sidewall of the collection channel, said collection channel can also be formed at least in part by at least one depression that extends into the supporting surface. More particularly, this depression can form at least one capillary channel. By way of example, this depression can be an elongate groove, flute or similar depression, with an e.g. rectangular cross section, a polygonal cross section, a round cross section or else a triangular cross section or a cross section with a different design in a sectional plane perpendicular to the supporting surface.

As illustrated above, the control part can, in particular, have a multi-part design and can have at least one disposable and at least one reusable. Thus, the base part can be part of the disposable, as can, optionally, the at least one fixing element, for example the at least one plaster, as well. The control part can additionally also have at least one reusable, for example at least one actuation unit. This actuation unit can, in particular, be connectable to the base part, for example by means of at least one force-fit and/or at least one interlocking connection. To this end, the base part and/or the actuation part can have at least one connection element in order to produce a connection of the aforementioned type. In particular, the base part and the actuation part can be connected to form a common control part with a common housing, which can for example have a substantially media-tight, e.g. moisture-tight, design. By way of example, the base part and the actuation part can be interconnected by means of at least one plug-in connection, which can also comprise an electrical plug-in connection. By way of example, this allows at least one electrical energy reservoir, for example at least one battery, to be arranged in the base part, which electrical energy reservoir can supply at least one electronic element in the actuation unit with electrical energy.

The actuation unit and the base part preferably are reversibly interconnectable in the sense that the base part is preferably part of a disposable, i.e. a single-use part, which can for example be replaced after one service life of the functional element. Accordingly, a base part can be embodied as a disposable which can be used as a consumable in a medical device as per one or more of the above-described embodiments. The base part is provided for use in a medical device, wherein use can be made in particular of a medical device as per the description above, and so reference can be made to the above description in respect of possible embodiments of this medical device. However, in principle, other embodiments are also possible. The base part is designed to be applied on a body surface of a user as part of at least one control part of the medical device. At least one functional element, which can be inserted into a body tissue of the user at at least one insertion site, can be connected to the control part, more particularly to the base part. To this end, the base part can for example comprise at least one connection element, for example a connection element for a force-fit and/or interlocking connection with the insertable functional element. However, alternatively, or in addition thereto, other types of connection are also possible. The functional element is designed to carry out at least one medical function. The functional element can also be designed integrally with the base part, i.e. it can also be permanently connected to the base part. The base part has at least one supporting surface, which faces the body surface. Furthermore, the base part has at least one collection channel for collecting bodily fluid emerging from the insertion site. Reference can be made to the description above in respect of further possible embodiments.

The above-described medical device and the above-described base part have a number of advantages over known medical devices and components thereof. Thus, contrary to the prior art cited above, bodily fluid emerging from the insertion site in particular is collected in the collection channel. However, the emergence of additional bodily fluid from the body tissue is not forced. Furthermore, the medical device, more particularly the base part, can have a very small design because the collection channel fundamentally requires no additional installation space. The collection channel, which is formed in the base part, can be embodied as a separate channel, independently of the sensor and/or the cannula or the functional element, and can for example be handled and/or produced separately. In particular, the collection channel can be formed in a body mount because the base part can be a component of an element of the medical device, which element can be applied to the body surface. The collection channel is suitable for guiding e.g. excessive blood and/or liquid away from the insertion site. By way of example, the collection channel can extend away from an opening in the supporting surface in both the right-hand and the left-hand directions, in which opening the functional element, for example the sensor, is held after the insertion. By way of example, blood or interstitial fluid, which can emerge from the insertion site during the insertion procedure, can thus be guided away from this emergence site and from the electrical contacts in the vicinity thereof, in particular in order to avoid leakage currents. This also increases the functional reliability of the medical device because, in particular, leakage currents, creepage currents or other electrical uncertainties and malfunctions can be reliably avoided. At the same time, the separate embodiment of the collection channel, which is preferably separate from the functional element and preferably separable from the functional element, can ensure a replaceability of the collection channel, for example within the scope of replacing the disposable. Accordingly, it is possible to ensure a targeted and hygienic disposal of the bodily fluid. In particular, the at least one collection channel can be embodied as a capillary gap between the supporting surface of the base part, which can more particularly be embodied as a base plate, and the at least one fixing element, for example the plaster, and this capillary gap can ensure that blood and/or other bodily fluids are guided away in a targeted fashion from critical components of the medical device, for example from a sealing system, which seals an evaluation unit and the base part with respect to one another, and/or from electrical contacts of the functional element, for example the sensor.

Thus, in particular, this can prevent bleeding at the insertion site from contaminating the seals and/or the electrical contacts of the medical device after the functional element was inserted. This can prevent frequent replacing of the body mount, which leads to a cost advantage. Furthermore, it is also possible to prevent unnoticed bleeding, or other emerging bodily fluids that remain unnoticed by the user, from resulting in the occurrence of leaks in the medical device, more particularly in the control part, and/or short circuits or creepage currents in the electrical contact. In particular, the collection channel can furthermore also reliably prevent a contamination of a reusable, e.g. an evaluation unit, by the bodily fluids. Furthermore, other contaminations can also be reliably prevented or at least be reduced, for example crusts from dried-on bodily fluid, which could otherwise also cause hygienic problems. Hence the embodiment according to the invention can make a significant contribution to improving the hygienic conditions of the medical device.

BRIEF DESCRIPTION OF THE DRAWINGS

Further features of the present invention, which can be implemented individually and also in any combination, emerge from the following description of preferred exemplary embodiments, which are illustrated in the figures and which can be implemented individually or in any combination. However, the invention is not restricted to the exemplary embodiments. Here, the same reference signs in the individual figures denote identical or functionally identical elements, or elements that correspond in respect of their function.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

FIGS. 1-5 illustrate different components of a medical device 110 for carrying out at least one medical function, to which reference is made collectively in the following text.

Figure 1:
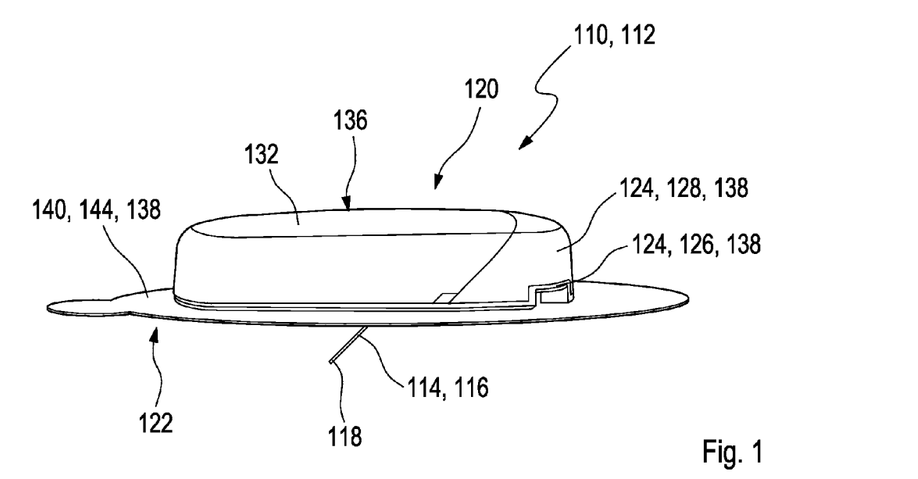
FIG. 1 is a side perspective view of an exemplary embodiment of a medical device according to the invention.

FIG. 1 shows this medical device 110 in a perspective illustration from the side. In this exemplary embodiment, the medical device 110 is designed as a sensor device 112 and is designed for long-term measurements of an analyte concentration in a body tissue of a user, for example for long-term measurements of blood-glucose levels. To this end, the sensor device 112 comprises at least one insertable functional element 114 in this case the form of an insertable sensor element 116, which can be inserted into the body tissue with an insertable end 118. By way of example, two or more electrodes are arranged at the insertable end 118 in order to be able to determine the analyte concentration by electrochemical means.

Figure 2:
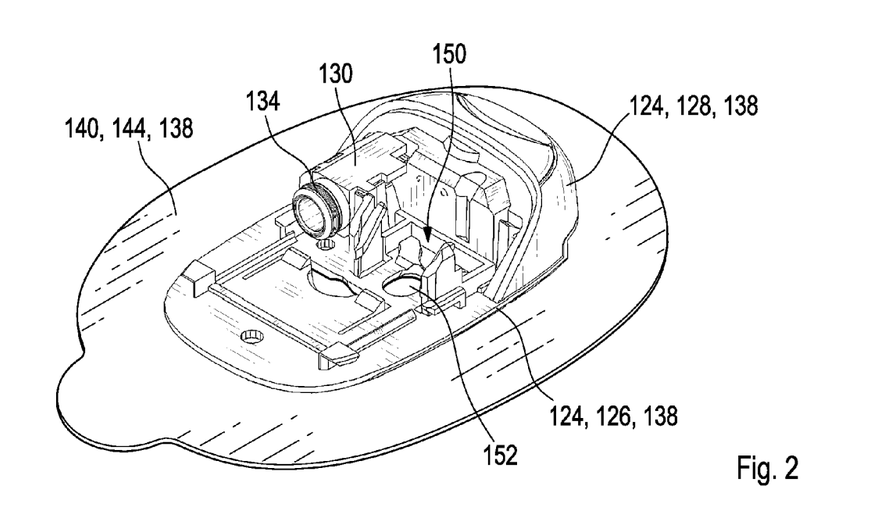
FIG. 2 is a perspective view of a base part of the medical device of FIG. 1.

In the illustrated exemplary embodiment, the medical device 110 furthermore has a control part 120, which is illustrated in FIG. 1 and which, in the inserted state of the sensor element 116, is arranged outside of the body tissue on a body surface of the user and has a side 122 facing the body surface. The control part 120 comprises a base part 124, which is often also referred to as a base plate 126 or which can comprise a base plate 126. By way of example, the base part 124 can comprise a battery housing 128 for holding one or more electrical energy sources or reservoirs. Furthermore, as shown in FIG. 2, the base part 124 can also comprise at least one connection element 130, by means of which the base part 124 can be connected to at least one actuation unit 132 of the control part 120, for example by means of a plug-in connection. The connection element 130 (wherein provision can also be made for a plurality of connection elements) can in particular comprise at least one sealing element 134, for example at least one 0-ring, in order to ensure a moisture-tight embodiment of the connection between the base part 124 and the actuation unit 132.

By way of example, the actuation unit 132 can comprise one or more electrical actuation and/or evaluation components in order to be able to acquire and/or store and/or at least partly evaluate signals from the sensor element 116. Thus, for example, at least one potentiostat can be provided in the actuation unit 132 in order to carry out electrochemical measurements by means of the sensor element 116. The actuation unit 132 can accordingly be embodied as, for example, a "reusable" 136 and can be used for at least two, preferably at least 10 measurement procedures, which can each take a number of days, a number of weeks or even a number of months. By contrast, the base part 124 is a component of a disposable 138, which is illustrated in FIG. 2 and which, in particular, can also be referred to as a so-called "body mount." The latter can, in addition to the base part 124, furthermore comprise at least one fixing element 140, which is arranged between a supporting surface 142 facing the body surface of the user (see the plan view in FIG. 4 and the side view of the base part 124 in FIG. 5). By way of example, this fixing element 140 can wholly or partly be embodied as a plaster 144.

Figure 3:
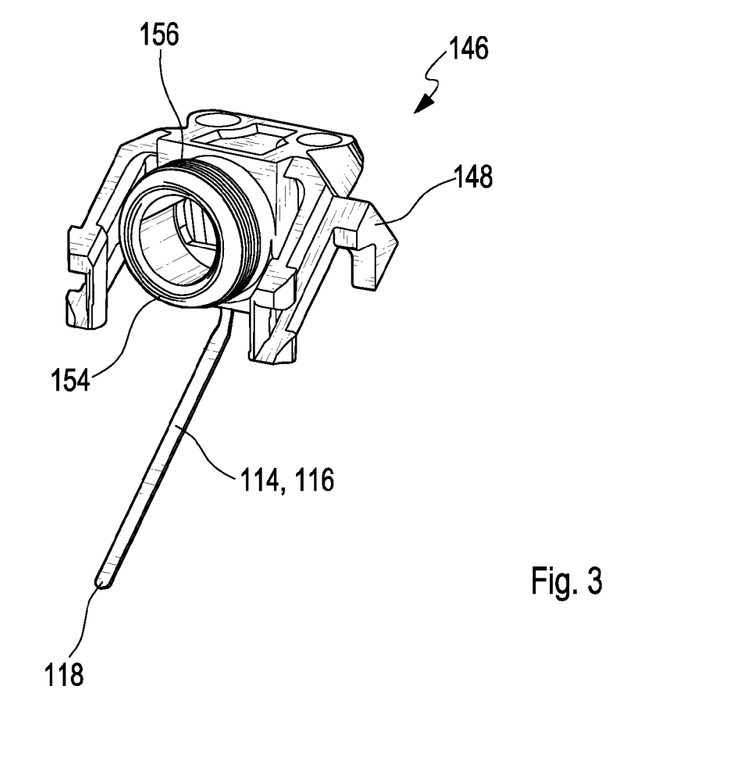
FIG. 3 is a perspective view of a sensor unit to be inserted into a medical device as per FIG. 1.

A sensor unit 146 can be connected to the control part 120, more particularly to the base part 124 in the present example. This sensor unit 146 is shown in a perspective illustration in FIG. 3. In addition to the sensor element 116, unit 146 comprises a sensor mount 148, which can be connected to a corresponding mount 150 in the base part 124 during the insertion, for example in an interlocking and/or force-fit fashion. During this insertion, which is brought about for example by means of at least one set of insertion instruments and/or at least one insertion cannula and/or insertion needle, the sensor element 116 is pushed through an opening 152 in the base part 124 and is inserted into the body tissue such that an insertion site (not illustrated in the figures) is arranged within the opening 152. In the process, the sensor mount 148 is connected to the mount 150. FIG. 3 shows that the sensor mount 148 also has a connection element 154, which in turn has a sealing element 156. When the sensor mount 148 is connected to the base part 124, i.e. after the insertion procedure, the element completed by then thus comprises the sensor unit 146 in addition to the base part 124 and the fixing element 140 as a collective module, which is subsequently connected to the actuation unit 132.

Figure 4:
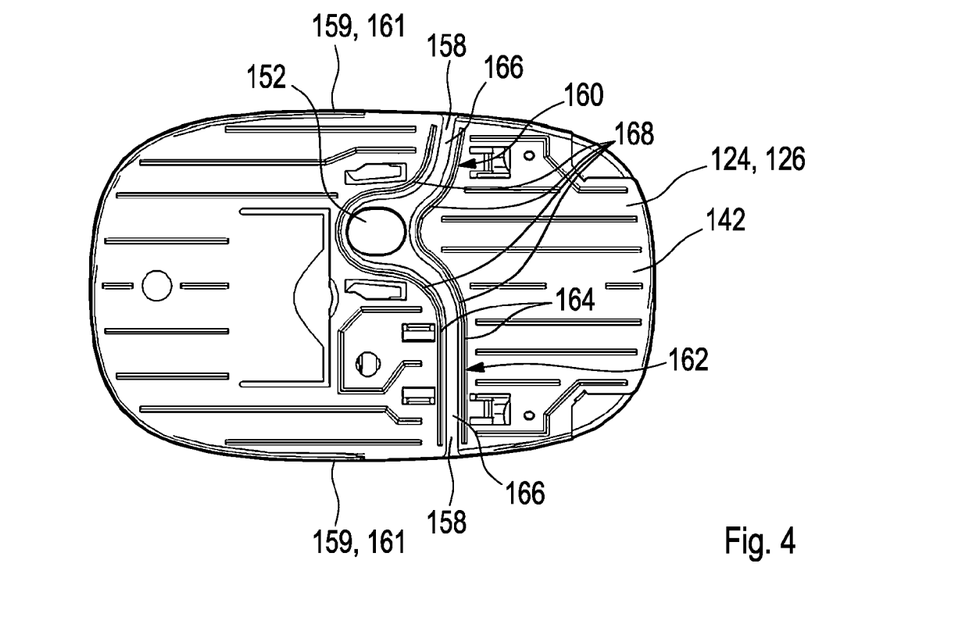
FIG. 4 is a bottom view of a base part of the medical device of FIG. 1.
Figure 5:
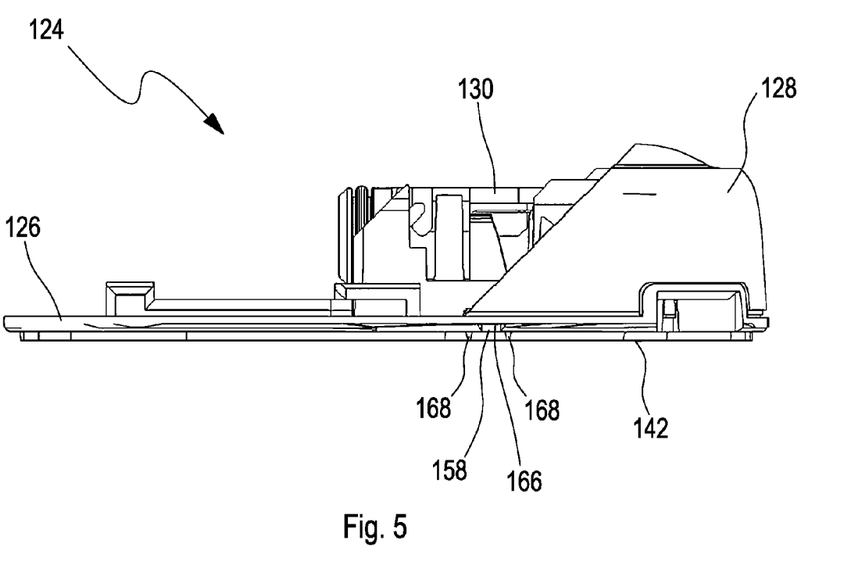
FIG. 5 is a side view of the base part of the device as per FIG. 1.

As described above, the base part 124, in exemplary embodiments, comprises at least one collection channel for collecting bodily fluids. This collection channel is visible in a plan view on the supporting surface 142 as per FIG. 4 and in a side view of the base part 124 in FIG. 5, and denoted therein by the reference numeral 158. In the illustrated exemplary embodiment, the collection channel 158 extends on the supporting surface 142 on both sides of the opening 152 and has two arms 160, 162. By way of example, the collection channel 158 can for example extend away from the opening 152 towards an outer edge 159 of the base part 124 at a border 161 of the supporting surface 142. Away from the opening 152, the collection channel 158 is embodied as a channel with substantially parallel sidewalls 164. On the one hand, these sidewalls 164 are formed by virtue of the fact that the collection channel 158 comprises a depression 166 in the form of a groove, which extends into the supporting surface 162. However, alternatively, or in addition thereto, the collection channel 158 can also, wholly or partly, be formed by virtue of the fact that provision is made for elongate projections 168, which can likewise form the sidewalls 164 of the collection channel 158 and which can for example, as shown in FIG. 4, wholly or partly surround the opening 152. Thus the sidewalls 164 can have a stepped design. The aforementioned preferred widths of the collection channel 158 can then, for example, refer to a mean width. However, in principle, other embodiments of the collection channel 158 are also possible.

EXAMPLE

A medical device 118 as per the exemplary embodiment illustrated in FIGS. 1-5 was tested in a practical trial. In the process, use was made of dummy sensor elements 116 with a geometry that can be used in practice, and also artificial skin and artificial blood with 150 ml/dl glucose. A digital microscope and a video camera were used to observe the processes in the region of the insertion site. The trials examined whether excess blood is discharged after the insertion via the collection channel 158, which, like a capillary, can for example be produced in the base part 124 during an injection molding process. Here, the base part 124 was designed as a rapid prototyping part and provided with a collection channel 158 in the form of a capillary gap. The plaster 144 was stuck onto the supporting surface 142. In the process, the capillary gap of the collection channel 158 is bonded in the region of its border, but it is not sealed.

The body mount produced thus was stuck onto the artificial skin, and this trial arrangement was placed vertically, as is the case, for example, for a vertically standing user who has a sensor element 116 inserted into the abdominal region. A syringe with a cannula attached thereto was subsequently filled with artificial blood. The syringe pierced the artificial skin from the side of the artificial skin lying opposite to the control part 120, and so the artificial blood could be filled into the insertion bore of the body mount. A sensor was subsequently inserted. Artificial blood was thereupon injected manually into the insertion site at a slow velocity, which was estimated to be approximately 5 μl/s. The blood flowed downward along the masked collection channel 158 and onto the plaster 144 on the underside of the base plate 126.

After this dose, the sensor plug, i.e. the connection through the connection element 154 in FIG. 3, was examined for blood contamination. In the process, no blood was discovered in particular at the sealing element 156, i.e. the O-ring for example, and in the region of the electrical contact of the sensor element 116, which constitute particularly critical sites. Blood remains could only be identified on the sensor element 116 itself. These trials showed that the discharge of excess blood through the collection channel 158 works in principle. This is an advantage for the user who does not need to replace the entire body mount as per FIG. 2, even in the case of strong bleeding. This results in a cost advantage for the user, and the sensor element 116 does not have to be inserted again.

Whether the collection channel 158 actually develops capillary forces or whether there merely is a discharge of blood or other bodily fluids e.g. as a result of gravity is immaterial. Collection channels 158, which also develop a capillary effect, lend themselves to lying patients in particular, because gravity plays a smaller role in this case. However, in the main usage position, in which the supporting surface 142 is vertical, capillary effects can also occur in principle, but the main effect in this case could be as a result of gravity. Hence, it is particularly advantageous in the illustrated medical device 110, and also in other exemplary embodiments of the medical device 110, if the collection channel 158, or at least one of the collection channels 158 (if more than one is provided) has at least one directional component towards the surface of the Earth such that bodily fluid driven by gravity can be discharged through this collection channel 158.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCES

110 Medical device
112 Sensor device
114 Functional element
116 Sensor element
118 Insertable end
120 Control part
122 Side facing the body surface
124 Base part
126 Base plate
128 Battery housing
130 Connection element
132 Actuation unit
134 Sealing element
136 Reusable
138 Disposable
140 Fixing element
142 Supporting surface
144 Plaster
146 Sensor unit
148 Sensor mount
150 Mount
152 Opening
154 Connection element
156 Sealing element
158 Collection channel
159 Edge
160 Arm
161 Border
162 Arm
164 Sidewalls
166 Depression
168 Projection

What is claimed is:

1. A medical device for carrying out at least one medical function, comprising:
   a control part which can be applied to a body surface of a user; and
   a functional element that is connectable to the control part, the functional element being insertable into body tissue for carrying out a medical function;
   wherein, the control part comprises a base part having a support surface configured to face the body surface, the base part comprising at least one collection channel for collecting bodily fluid emerging from the insertion site and conveying excess bodily fluid in a direction substantially parallel to the support surface.

2. The medical device of claim 1, wherein the collection channel is at least partly formed in the support surface.

3. The medical device of claim 1, further comprising at least one fixing element positioned on the support surface for adhering the base part to the body surface.

4. The medical device of claim 3, wherein the fixing element comprises a plaster.

5. The medical device of claim 3, wherein the fixing element at least partly covers the collection channel.

6. The medical device of claim 1, wherein the functional element comprises: a sensor element for acquiring at least one body state of the user, a sensor element for acquiring at least one analyte in a bodily fluid of the user, an actuator for influencing at least one body state of the user, or a medication device for applying at least one active ingredient into a body tissue of the user.

7. The medical device of claim 1, wherein the collection channel ends at an edge of the supporting surface.

8. The medical device of claim 1, further comprising an opening in the support surface, wherein the functional element is insertable into body tissue through the opening and the collection channel extends away from the opening.

9. The medical device of claim 8, wherein the collection channel extends away from the opening in at least two directions.

10. The medical device of claim 8, wherein the collection channel extends to a border of the support surface.

11. The medical device of claim 1, wherein the collection channel comprises a capillary channel.

12. The medical device of claim 1, wherein the collection channel has a depth direction that is substantially perpendicular to the support surface, the depth of the collection channel being about 0.05 mm to 3 mm.

13. The medical device of claim 12 wherein the collection channel has a depth direction that is substantially perpendicular to the support surface, the depth of the collection channel being about 0.1 mm to 2 mm.

14. The medical device of claim 13, wherein the collection channel has a depth direction that is substantially perpendicular to the support surface, the depth of the collection channel being about 0.2 mm to 1 mm.

15. The medical device of claim 1, wherein the collection channel has a width at its narrowest point of about 0.2 mm to 10 mm.

16. The medical device of claim 15, wherein the collection channel has a width at its narrowest point of about 0.3 mm to 5 mm.

17. The medical device of claim 16, wherein the collection channel has a width at its narrowest point of about 0.5 mm to 2 mm.

18. The medical device of claim 1, wherein the base part has at least one projection extending away from the support surface, wherein the projection forms at least part of at least one sidewall of the collection channel.

19. The medical device of claim 1, wherein the collection channel comprises a depression extending into the support surface.

20. A method of using a medical device of the type having a functional element that is insertable into the skin of a patient, comprising:
providing a control part having a support surface configured to contact a body surface, the support surface having a collection channel;
adhering the support surface to the body surface;
inserting the functional element through an opening in the control part into the body surface;
connecting the functional element to the control part; and
moving bodily fluid that emerges from the body surface away from the opening through the collection channel in a direction substantially parallel to the support surface.

21. The method of claim 20, wherein the step of moving bodily fluid comprises moving the bodily fluid away from the opening through the collection channel in at least two directions.

22. The method of claim 21, further comprising using gravity to move the bodily fluid through the collection channel.

23. The method of claim 20, further comprising using capillary forces to move the bodily fluid through the collection channel.

24. The method of claim 20, comprising at least partially covering the collection channel with a plaster that adheres the support surface to the body surface.

25. The method of claim 20, further comprising collecting bodily fluid with the functional element.

26. The method of claim 25, further comprising analyzing the bodily fluid collected with the functional element for the presence or concentration of an analyte.

27. The method of claim 26, wherein the analyte is glucose and the collecting and analyzing of the bodily fluid is performed at periodic intervals while the control portion remains adhered to the body surface.

28. The method of claim 20, further comprising delivering a medicine through the functional element.

29. A disposable base part for use with a medical device, comprising:
a connector for removably connecting the base part to a re-usable control part;
a support surface;
a fixing element configured to adhere the support surface to a patient's skin;
an opening adapted to receive therethrough a functional element configured to be inserted into the patient's skin for carrying out a medical function; and
at least one collection channel extending away from the opening, whereby excess bodily fluid emerging from the patient's skin can be directed away from the opening through the collection channel in a direction substantially parallel to the support surface.

30. The disposable base part of claim 29, wherein the collection channel extends away from the opening in at least two directions.

31. The disposable base part of claim 29, wherein the fixing element comprises a plaster that at least partially covers the collection channel.

32. The disposable base part of claim 29, wherein the collection channel is dimensioned as a capillary channel.

33. A medical device for carrying out at least one medical function, the device comprising:
a functional element insertable into body tissue for carrying out a medical function; and
a control part adapted to be applied to a body surface of a user, the functional element being connectable to the control part;
wherein the control part comprises a base part having a support surface configured to face the body surface, the support surface defining an opening adapted to receive therethrough the functional element for insertion into body tissue, the support surface further defining an edge forming an outer perimeter of the support surface; and
wherein the support surface further defines at least a portion of at least one collection channel, the at least one collection channel extending away from the opening toward the edge of the support surface wherein the collection channel is adapted to collect excess bodily fluid emerging from the body surface proximate the opening and convey the excess bodily fluid in a direction substantially parallel to the support surface away from the opening.

34. The medical device of claim 33 wherein the support surface includes a depression, the depression defining at least a portion of the at least one collection channel.

35. The medical device of claim 33 further comprising a projection extending outwardly from the support surface and wherein the projection defines at least a part of the collection channel.

36. The medical device of claim 33 wherein the at least one collection channel extends to the edge of the support surface.

* * * * *